United States Patent [19]

Leonard et al.

[11] Patent Number: 4,820,525

[45] Date of Patent: Apr. 11, 1989

[54] TRANSDERMAL DRUG DELIVERY SYSTEM

[75] Inventors: Thomas W. Leonard, Plattsburgh; Robin P. Enever, Rouses Point; Karol K. Mikula, Morrisonville, all of N.Y.

[73] Assignee: American Home Products Corporation (Del.), New York, N.Y.

[21] Appl. No.: 97,998

[22] Filed: Sep. 17, 1987

[51] Int. Cl.$^4$ ............................................. A61K 9/70
[52] U.S. Cl. ................................... 424/486; 424/449; 604/307
[58] Field of Search ............... 604/307; 424/444, 448, 424/449

[56] References Cited

U.S. PATENT DOCUMENTS

| | | | |
|---|---|---|---|
| 3,972,995 | 8/1976 | Tsuk et al. | 128/156 |
| 4,460,368 | 7/1984 | Allison et al. | 424/449 |
| 4,627,429 | 12/1986 | Tsuk | 128/156 |
| 4,649,075 | 3/1987 | Jost | 424/449 |
| 4,687,481 | 8/1987 | Nuwayser | 424/449 |

*Primary Examiner*—William R. Dixon, Jr.
*Assistant Examiner*—David M. Brunsman

[57] ABSTRACT

The invention provides a transdermal/transmucosal pharmaceutical delivery system having an improved drug reservoir comprising a thin layer of foamed material made from high molecular weight polyethylene, the foamed material having a void volume of at lesat 20% per unit of surface area and a narrow pore size variation per unit of surface area.

5 Claims, 4 Drawing Sheets

TRANSDERMAL DRUG DELIVERY SYSTEM

BACKGROUND OF THE INVENTION (a) Field of the Invention

This invention relates to a novel transdermal or transmucosal drug delivery system and dosage form to deliver a pharmaceutical substance in a controlled fashion for an extended period of time in an efficient manner. More particularly this invention relates to a dosage form comprising a polyethylene material having particular physical characteristics impregnated with a liquid or semi solid drug formulation.

(b) Prior Art

Transdermal and transmucosal delivery systems for pharmaceutical substances are well known in the art. Most such delivery systems comprise a dosage form to deliver the substance in a controlled manner as part of an enclosing bandage or application means for protecting the dosage form from the atmosphere during storage and means for affixing the dosage form to the patient's skin after application. A particularly effective transdermal delivery system is that described in Tsuk U.S. Pat. No. 4,627,429 and a particularly effective transmucosal delivery system is that described in Tsuk U.S. Pat. No. 3,972,995, each of which patents is incorporated herein by reference in its entirety.

Each of the Tsuk patents describes a dosage form to be included in the drug delivery system, the dosage form comprising a porous material such as polyurethane foam. It has been found that dosage forms made from polyurethane are subject to degradation from certain solvents used for medications and, not being heat sealable, are difficult to attach to suitable backings.

Transdermal and transmucosal delivery systems generally comprise in addition to a disk shaped dosage form containing the medication an occlusive or protectant material applied to the back of the disk, usually be heat sealing, and an adhesive coating applied to the front of the disk or by a non-occlusive tape applied over the occlusive backing and extending beyond the perimeter of the disc.

THE INVENTION

The present invention is directed to a dosage form to deliver a pharmaceutical substance in a controlled fashion for an extended period of time in an efficient manner, the dosage form being a component of a delivery system such as those described in Tsuk U.S. Pat. Nos. 4,627,429 and 3,972,995. The dosage form comprises a polyethylene foamed material having particular physical characteristics including a void volume of at least about 20% to about 70% preferably about 35% to about 55% per unit of surface area and a pore size variation of 0-8 microns for the particular material. The void volume of at least about 20% per unit of surface area is large enough to hold sufficient drug formulation to provide a zero order driving force for a reasonably sized dosage form for the intended duration of application. The pore size in microns can be varied for a particular pharmaceutical substance between about 10 to 70 microns preferably about 20 to 50 microns so long as the pore variation for the particular polyethylene foamed material is within the range of 0-8 microns. The polyethylene foamed material is preferably in sheet or roll form having a thickness of about one thirty-second inch to one-sixteenth inch but may be cast or molded in dosage form size.

The advantages provided by the dosage form of the present invention include its heat sealability, its imperviousness to many medication solvents, its ability to absorb medications and its wicking action, and its ability to maintain good skin contact.

DETAILED DESCRIPTION OF THE INVENTION

Figure 1:
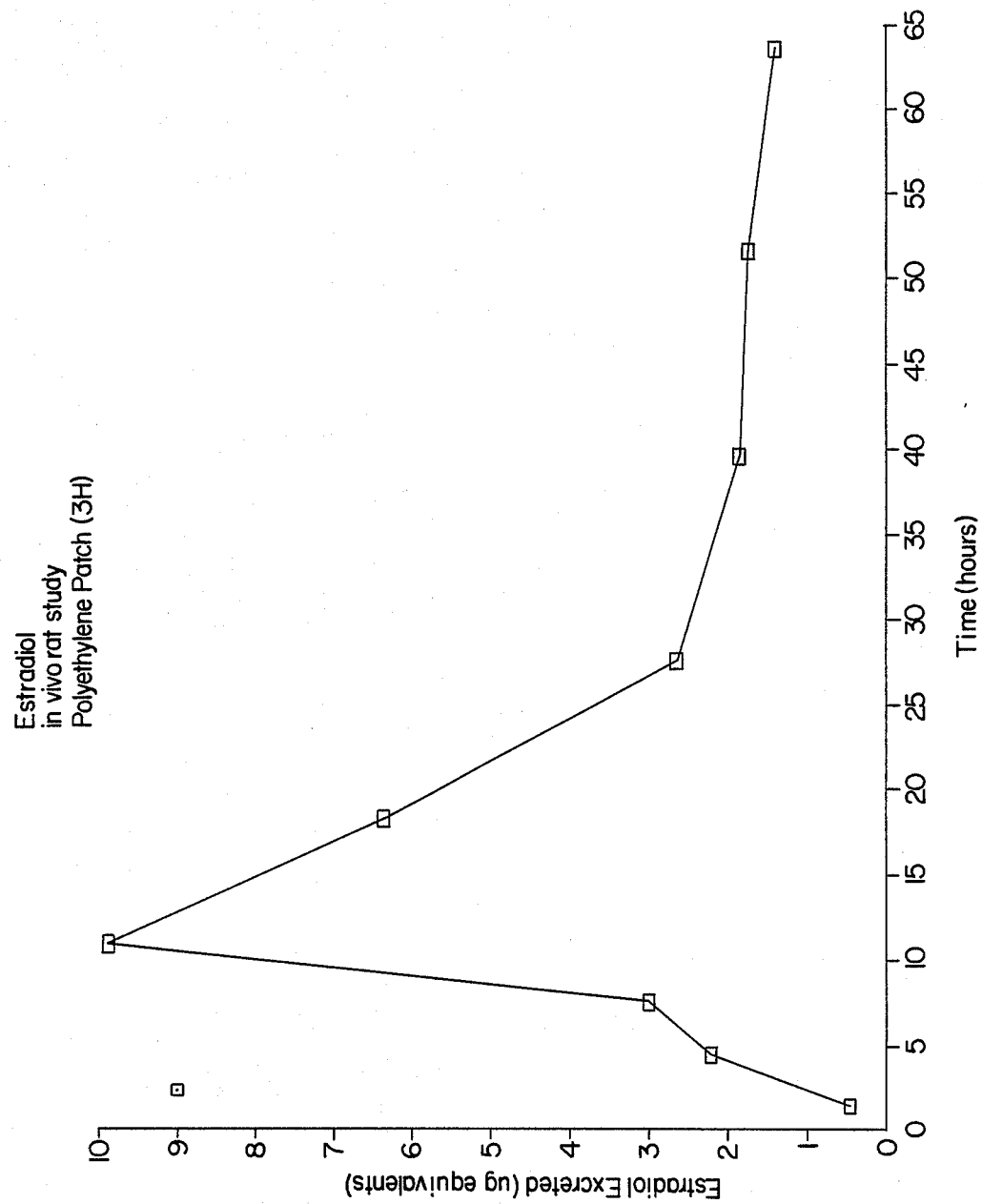
Figure 2:
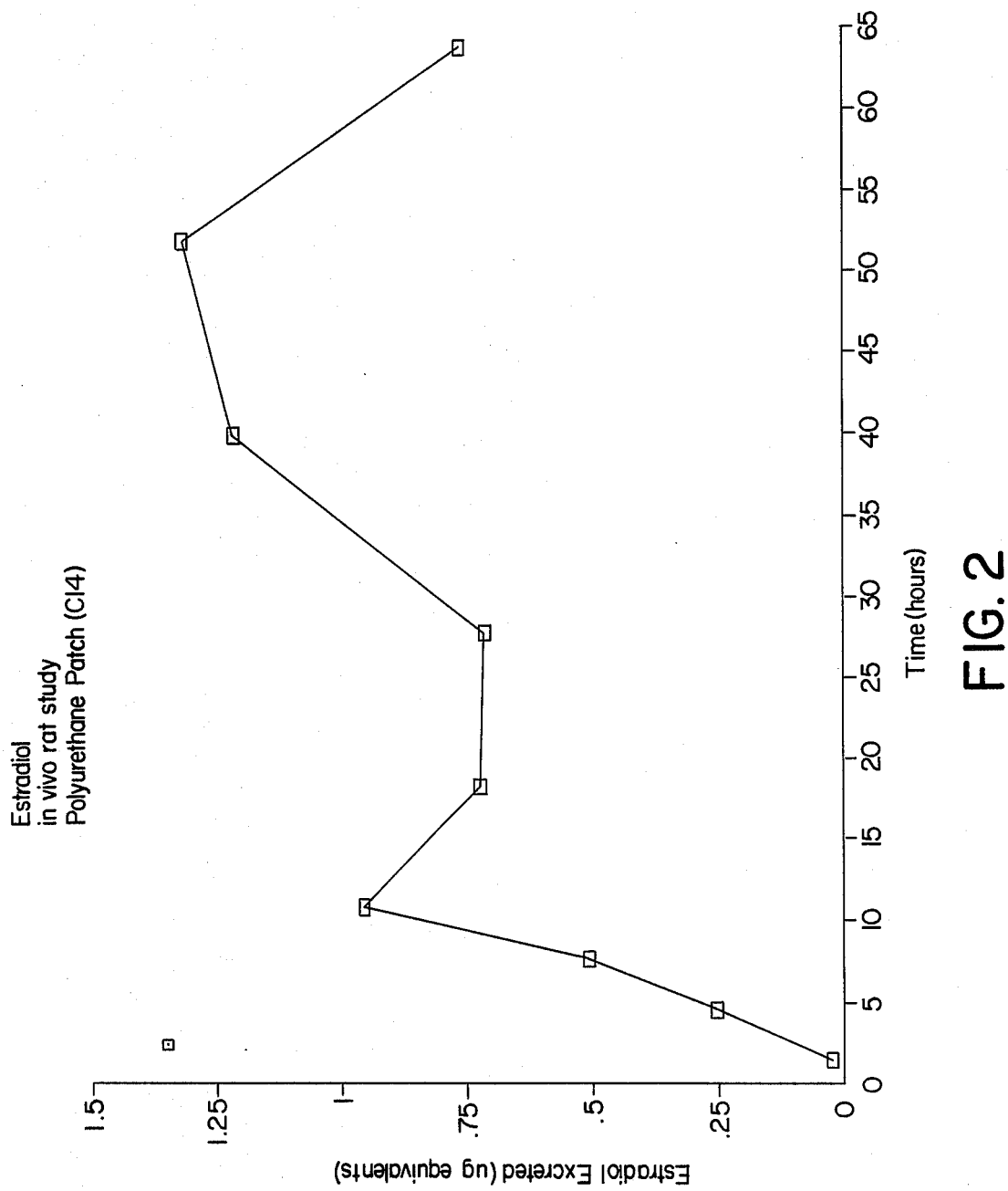
Figure 3:
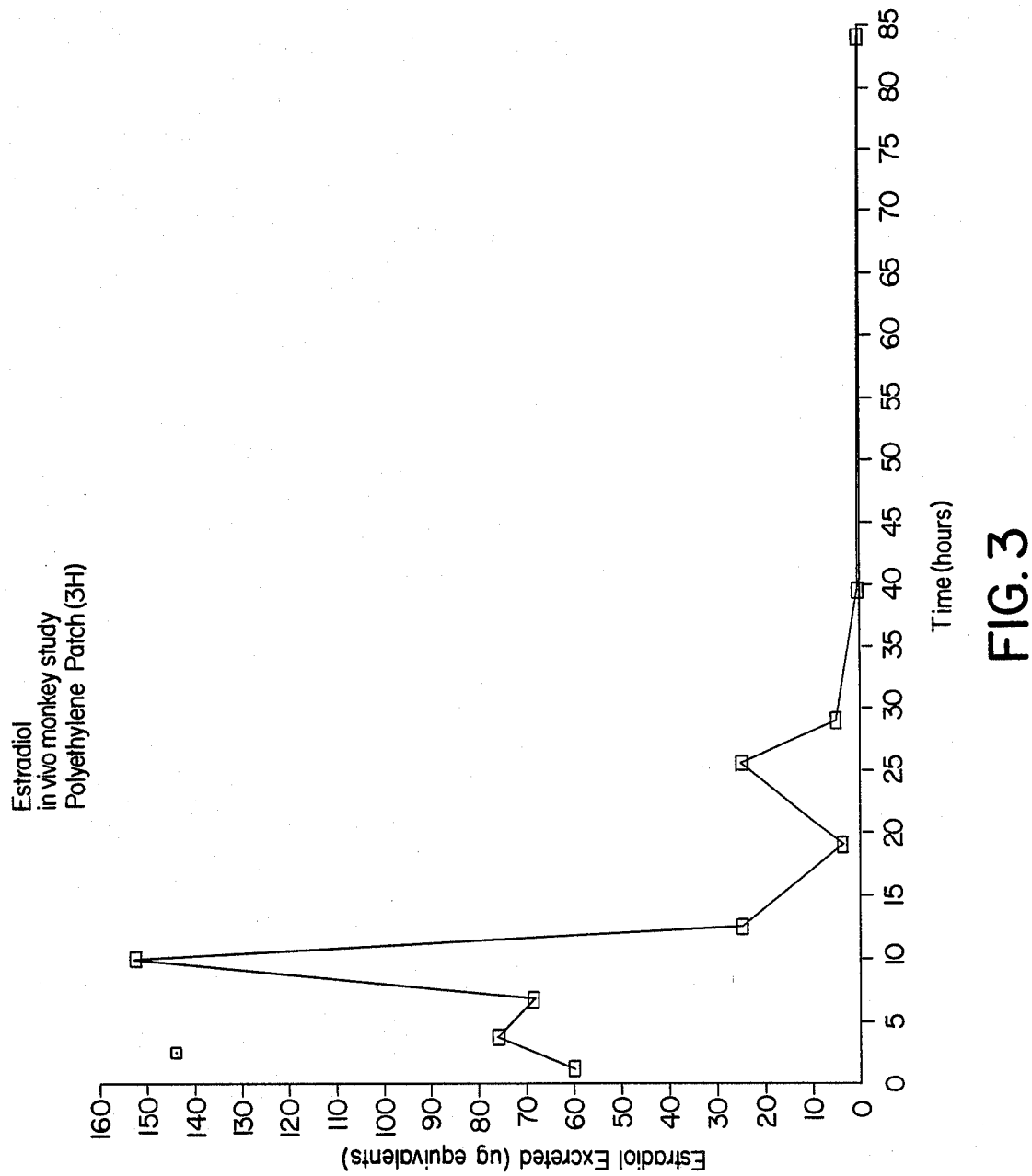
Figure 4:
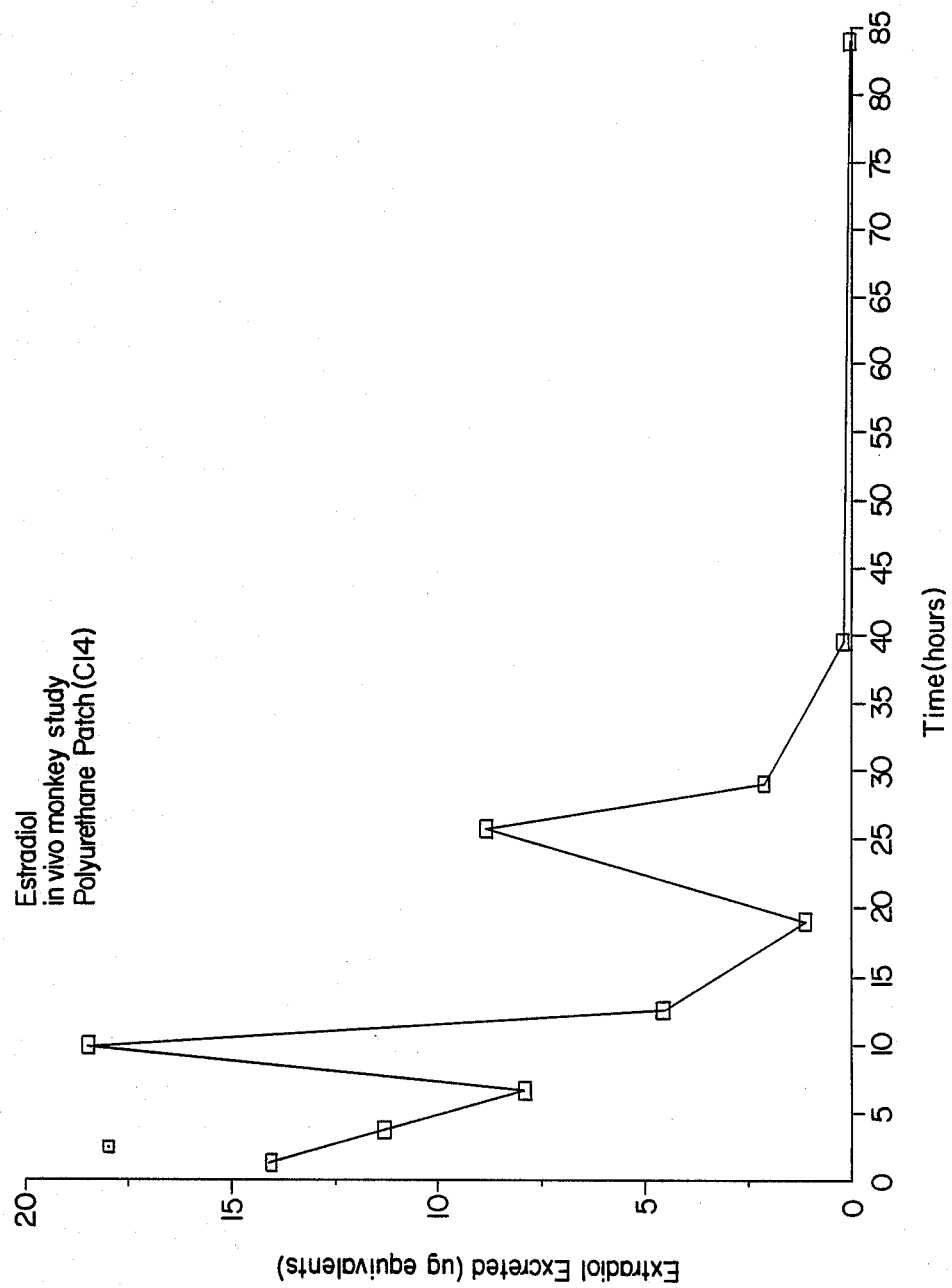

The polyethylene foamed material suitable for the dosage forms of this invention is available commercially in sheet form or roll stock, from which the dosage forms can be cut or punched, having a thickness varying from one-sixteenth inch to one thirty-second inch. The polyethylene foamed material can be made from ultra high molecular weight polyethylene or from high density polyethylene. Suitable polyethylene foam materials can be obtained from Porex Technologies Corporation of Fairburn, Ga. as Porex x-4900, a fine polyethylene foam made from ultra high molecular weight polyethylene having a void volume of 45% per unit of surface area, a 20-25 micron pore size and available in 12 inch square sheets having a thickness of one-sixteenth inch. Another foam material is Porox P-20, a polyethylene foam made from high density polyethylene having a void volume of 40% per unit of surface area, a 20-25 micron pore size and also available in 12 inch square sheets having a thickness of one-sixteenth inch. Other suitable polyethylene foam materials can be obtained from Chromex Corporation of Brooklyn, N.Y.

The polyethylene foam material can be heat-sealed to, for example, an aluminum foil laminate coated on its topside with a suitable heat-seal coating such as a coating of ethyl vinyl acetate, polyethylene or a polyvinylchloride. Aluminum foil laminates can be obtained from Meditect Division of Labeltape, Inc. of Grand Rapids, Mich.

The polyethylene foam material heat-sealed to the aluminum foil laminate can have applied to its obverse surface a suitable adhesive coated flannel-CEREX facestock, adhesive side up, and on top of the facestock a heavy weight white paper release liner. The flannel-CEREX facestock is a skin adhesive backed by a soft white fine textured non-woven fabric.

The effectiveness of the polyethylene dosage forms of the invention in transdermally delivering medication is shown in the following examples in comparison with polyurethane dosage forms.

In the examples menthol was employed as a penetration enhancer as disclosed and claimed in copending application Ser. No. 564,654, filed Dec. 22, 1983 of Andrew G. Tsuk. Other penetration enhancers can also be employed such as those described in U.S. Pat. Nos. 4,548,922 and 4,405,616.

EXAMPLE 1

Patches were prepared by attaching a 5.1cm$^2$ circular disk of polyethylene foam, 1/16" thick, 60% void volume, 40 to 45 $\mu$ diameter pore size, to a suitable nonporous adhesive coated tape, approximately 6 cm×6cm. Polyurethane foam patches were prepared similarly using a 1/32" thick foam, with 40 pores/linear inch. Estradiol formulation was prepared and divided into aliquots. One aliquot was spiked with H$^3$ labelled estradiol and 400 mg of the formulation was applied to each polyethylene patch. A second aliquot was spiked with C$^{14}$ labelled estradiol and 250 mg was applied to each polyurethane patch. This amount of formulation was sufficient to fill the void volume of each patch. One of each of the two patches was applied to backs of each of 10 male albino rats one day following clipping. Additional porous tape was used to hold the patches in place. The rats were placed in individual metabolism cages and urine was collected at 3, 6, 9, 12, 24, 31, 48, 55, and 72 hours after patch application. Patches were removed 24 hours after application and the treatment site was washed with soapy water, rinsed and dried. Urine samples were assayed for each radioactive isotope. Results from the study are presented in FIG. I and II and show the rate or excretion of 17-$\beta$-estradiol as a function of time. Each point is the average value for the 10 rats treated. These data indicate that the polyethylene disk is an efficient system for transdermal delivery of estradiol.

EXAMPLE 2

Two patches were similarly prepared to those in Example 1. However, an additional layer of foam adhesive tape was applied to non-porous tape and placed concentrically around the foam disk. Approximately 200 mg of $C^{14}$ labelled formulation was applied to the polyurethane disk and approximately 415 mg was applied to the polyethylene disk. One patch was applied to each arm of a rhesus monkey, in a region that had been clipped one day prior to the study. The monkey was restrained during the experiment. Urine samples were collected 2, 5, 8, 11, 14, 24, 27, 31, 48, 72 and 120 hours after treatment. The patches were removed 24 hours after treatment. Samples were assayed for $C^{14}$ and $H^3$ content by liquid scintigraphy. Results from the study are presented in FIG. III and IV and show the rate of excretion of 17-$\beta$-estradiol as a function of time. These data indicate that the polyethylene disk is an efficient system for transdermal delivery of estradiol.

EXAMPLE 3

Patches were prepared by attaching a 0.79cm$^2$ circular disk of 1/16" thick polyethylene foam to an occlusive plastic backing. Formulations were prepared, using the concentrations listed in Tables 1–4, and spiked with either $H^3$ labelled 17-$\beta$-estradiol or $H^3$ labelled estrone sulfate, or, in the albuterol formulation, left unlabelled. All formulations were applied to the polyethylene patches prior to the initiation of the experiment. Cadaver skin was obtained at autopsy and frozen until use, at which time it was dermatomed 250 microns thick. Mouse skin was excised from freshly killed nude mice. Both skins were mounted on the diffusion cell with the dermal surface towards the receiving fluid reservoir. The patches were placed on the skin so that the stratum corneum was in contact with the formulation.

The receiving fluid was phosphate buffer, pH 7.4, and was mechanically stirred and maintained at 32° C. The cadaver skin experiments ran for 48 hours, while the mouse experiments ran for 24 hours. Samples of the receiving fluid were taken by an automatic sampler and analyzed for drug content by either a liquid scintillation counter (Beckman 5800) or HPLC.

Results for all diffusion cells are shown in Tables 1–4. The steady state flux was determined by a least-squares best fit of the amount of drug diffused as a function of time, divided by the area of the patch. These data indicate that the polyethylene disk is an efficient system for transdermal delivery of 17-$\beta$-estradiol, estrone sulfate and albuterol.

TABLE 1

TRANSFER OF 17$\beta$-ESTRADIOL ACROSS NUDE MOUSE SKIN FROM POLYETHYLENE PATCHES

| Experiment # | Drug Transferred (mcg) | Steady State Flux (mcg/hr/cm$^2$) |
|---|---|---|
| 1 | 7.93 | .36 |
| 2 | 10.49 | .47 |
| 3 | 38.90 | 2.09 |
| 4 | 20.08 | 1.16 |
| 5 | 69.01 | 3.98 |
| 6 | 27.31 | 1.49 |
| Formulation: | 5% 17-$\beta$-estadiol 5% menthol 90% propylene glycol | |

TABLE 2

TRANSFER OF 17-$\beta$-ESTRADIOL ACROSS CADAVER SKIN FROM POLYETHYLENE PATCHES

| Experiment # | Drug Transferred (mcg) | Flux (mcg/hr/cm$^2$) |
|---|---|---|
| 1 | 4.74 | 0.08 |
| 2 | 7.63 | 0.15 |
| 3 | 15.85 | 0.39 |
| 4 | 17.23 | 0.81 |
| 5 | 6.73 | 0.21 |
| 6 | 29.33 | 1.07 |
| Formulation: | 5% 17-$\beta$-estradiol 5% menthol 90% propylene glycol | |

TABLE 3

TRANSFER OF ESTRONE SULFATE ACROSS CADAVER SKIN FROM POLYETHYLENE PATCHES

| Experiment # | Drug Transferred (mcg) | Steady State Flux (mcg/hr/cm$^2$) |
|---|---|---|
| 1 | 6.32 | .23 |
| 2 | 7.52 | .44 |
| 3 | 23.37 | 1.86 |
| 4 | 8.03 | .46 |
| 5 | 22.62 | 1.88 |
| 6 | 28.08 | 1.75 |
| Formulation: | 8.4% purified conjugated estrogen concentrate, of which 17.9% is estrone sulfate 62.7% propylene glycol 12.5% water 8.4% isopropanol 8.0% menthol | |

TABLE 4

TRANSFER OF ALBUTEROL ACROSS NUDE MOUSE SKIN FROM POLYETHYLENE PATCHES

| Experiment # | Drug Transferred (mcg) | Steady State Flux (mcg/hr/cm$^2$) |
|---|---|---|
| 1 | 236.29 | 27.37 |
| 2 | 241.09 | 25.74 |
| 3 | 247.69 | 28.92 |
| Formulation: | 10.0% albuterol 67.5% 2-(2-ethocyethoxy)ethanol 22.5% N—methyl-2-pyrrolidone | |

We claim:

1. In a transdermal/transmucosal pharmaceutical delivery system comprising a drug reservoir, an occlusive backing for the drug reservoir and means for adhesively applying the drug reservoir to the skin, the improvement which comprises using as the drug reservoir a dosage form consisting essentially of a thin layer of foamed material produced from high molecular weight/high density polyethylene, the foamed material having a void volume of at least about 20% to about 70% per unit of surface area and a pore size variation of from about 0 to 8 microns per unit of surface area, the pore size of the polyethylene foam being within the range of about 10 to 70 microns.

2. The transdermal/transmucosal delivery system of claim 1 wherein the foamed material has a void volume of at least about 35 to about 55% and a pore size within the range of about 20 to 50 microns.

3. The transdermal/transmucosal delivery system of claim 1 wherein the dosage form is a thin layer of foamed material produced from high molecular weight polyethylene, the foamed material having a void volume of about 45% per unit of surface area and a pore size of about 20–25 microns.

4. The transdermal/transmucosal delivery system of claim 1 wherein the dosage form is a thin layer of foamed material produced from high density polyethylene, the foamed material having a void volume of about 40% per unit of surface area and a pore size of about 20–25 microns.

5. The transdermal/transmucosal delivery, system of claims 2, 3 and 4 wherein the thin layer of foamed material is one thirty-second to one-sixteenth inch thick.

* * * * *